US006686751B1

(12) United States Patent
Saito et al.

(10) Patent No.: US 6,686,751 B1
(45) Date of Patent: Feb. 3, 2004

(54) METHOD AND APPARATUS FOR DETECTING NEGATIVE ION IN WATER

(75) Inventors: Takayuki Saito, Kanagawa (JP); Syu Nakanishi, Shizuoka (JP); Kanroku Chounan, Kanagawa (JP)

(73) Assignee: Ebara Corporation, Tokyo (JP)

( * ) Notice: Subject to any disclaimer, the term of this patent is extended or adjusted under 35 U.S.C. 154(b) by 0 days.

(21) Appl. No.: 09/926,195

(22) PCT Filed: Mar. 6, 2000

(86) PCT No.: PCT/JP00/01326

§ 371 (c)(1),
(2), (4) Date: Sep. 21, 2001

(87) PCT Pub. No.: WO00/57165

PCT Pub. Date: Sep. 28, 2000

(30) Foreign Application Priority Data

Mar. 24, 1999 (JP) .............................. 11/079008

(51) Int. Cl.[7] .............................. G01N 27/06; C25B 9/00
(52) U.S. Cl. ........................ 324/694; 324/439; 204/263; 205/789
(58) Field of Search ................................ 324/691, 694, 324/439, 722; 204/632, 263; 422/82.02; 205/742, 789

(56) References Cited

U.S. PATENT DOCUMENTS

| | | | | |
|---|---|---|---|---|
| 3,869,376 A | * | 3/1975 | Tejeda ........................ | 204/632 |
| 5,788,828 A | * | 8/1998 | Nakatsu et al. ............. | 204/632 |
| 6,274,019 B1 | * | 8/2001 | Kuwata ....................... | 204/632 |
| 6,328,885 B1 | * | 12/2001 | Srinivasan et al. ...... | 210/198.2 |
| 6,426,629 B1 | * | 7/2002 | Edgson et al. ............. | 324/439 |

FOREIGN PATENT DOCUMENTS

| | | |
|---|---|---|
| DE | P3217987 | 5/1982 |
| EP | 0777120 A2 | 6/1997 |
| JP | 01-228589 | 9/1989 |
| JP | 05-264393 | 10/1993 |
| JP | 06-011406 A | 1/1994 |

OTHER PUBLICATIONS

European Search Report dated Aug. 2, 2002.

* cited by examiner

*Primary Examiner*—Anjan K. Deb
(74) *Attorney, Agent, or Firm*—Westerman, Hattori, Daniels & Adrian, LLP

(57) ABSTRACT

The present invention provide a method and an apparatus for detecting anions in water which does not require replacement of ion exchange resins and the like and can perform precise measurement at low cost in a simple operation. The apparatus for detecting anions in water according to the present invention is an apparatus for detecting anions in water with the use of an electric conductivity cell and is constituted by an electrolyzer having an anode chamber having an anode plate and a cation chamber having a cathode plate via a cation exchange membrane, a direct-current power unit for applying a direct-current voltage between the anode and the cathode of the electrolyzer and an electric conductivity cell for measuring the electric conductivity of a sample water, and a flow passage for introducing a sample water into the anode chamber and a treated water flow passage for discharging the treated water which has been subjected to electrolytic treatment in the anode chamber which are connected to the anode chamber, respectively, and the treated water flow passage being connected to the cathode chamber via an electric conductivity cell.

5 Claims, 2 Drawing Sheets

METHOD AND APPARATUS FOR DETECTING NEGATIVE ION IN WATER

FIELD OF THE INVENTION

The present invention relates to the detection of anions in water and particularly, it relates to an apparatus for detecting anions typified by a chlorine ion, which can sense the leakage of a cooling water (seawater) of a condenser in a thermal power station and a nuclear power station.

BACKGROUND OF THE INVENTION

Heretofore, in a thermal power station or a nuclear power station, as shown in FIG. 2, circulation of water is performed in such a manner that the high temperature, high pressure steam generated in a boiler 21 is led to steam turbines 23 and 25, and the steam discharged from the steam turbine 25 is condensed into water in a condenser 27 and this condensed water is again used as the boiler feedwater. Impurities such as corrosion products are accumulated in the circulation water and accordingly, a purifying apparatus (condensed water demineralizer) 29 is installed. Since the condenser 27 in this circulatory system is under reduced pressure at the steam side and uses seawater 28 as the cooling water, when a pinhole is formed in capillaries of the condenser, the seawater enters the: steam side to remarkably increase the concentration of salts. As the result, the load of the condensed water demineralizer 29 is increased, and increased amounts of leaked seawater exceed the tolerance limits of this demineralizer 29. Then, it becomes necessary to detect the seawater leakage by a salt detecting instrument.

For the detection of seawater leakage a method of measuring an electric conductivity, a sodium monitor, an atomic absorption spectrometry and the like have been employed.

The method of measuring a specific resistivity or an electric conductivity needs cation exchange resins. The reason is that in order to inhibit the corrosion in the system, ammonia and hydrazine are normally added to a circulating water in amounts so as to adjust the ammonia concentration as $NH_4^+$ to about 1 ppm and the hydrazine concentration as $N_2H_4$ to about 100 ppb and the specific resistivity of the circulating water is low and the electric conductivity is high. Accordingly, the change in the electric conductivity of the circulating water by a slight increase of the salt concentration due to seawater leakage is very small, which makes it difficult to detect the seawater leakage. Here, the conventional method comprises, first, passing the circulating water through regenerative cation exchange resins to remove ammonia and hydrazine of cations which are originally present in the circulating water and cation components such as a sodium ion in the major component of NaCl having been mixed thereinto by the seawater leakage and then, measuring the specific resistivity (acid specific resistivity) or the electric conductivity mainly by HCl.

Further, the sodium monitor uses an ion-selective glass electrode and accordingly, the sensitivity in a low concentration region deviates from the Nernst equation to become lower by decrease in the electromotive force. Moreover, as a potassium chloride solution is used as the electrode solution of the reference electrode, a plus error sometimes occurs by the diffusion of a potassium ion to the sample water side. In addition, the surface of the electrode is fouled with fine particles of iron oxides and hydroxides which are called as cruds to lower the sensitivity and the like. Thus, the sodium monitor has the above described disadvantages.

With respect to the atomic absorption spectrometry and the like, at present there is no instrument for analysis of the portable type which can be set at the site and accordingly, a technique of sampling a sample water to be analyzed and bringing it to a chemical laboratory for analysis has to be taken and the circulating water cannot constantly be monitored. An instrument for ion chromatographic analysis is comparatively small but the preparation of reagents and the like take much time and moreover, the instrument is expensive as in the atomic absorption spectrometry. The method of measuring an acid electric conductivity needs cation exchange resins as described above. When a predetermined amount of ions is adsorbed on these resins, the resins cease to exhibit their adsorption capacity and need regeneration or replacement of the resins and thus, such operations and the cost of the resins become a problem.

As the apparatus for detecting anions in water which solves the above described problems, the inventors of the present invention have previously proposed an apparatus for detecting anions in water which utilizes electric continuous ion exchange equipment [Japanese Patent Publication (Kokai) JP-A-9-210943]. This equipment is provided with a chamber for dealkalization chamber which is partitioned with two cation exchange membranes between an anode chamber and a cathode chamber and filled with cation exchangers in electric continuous ion exchange equipment and an electric conductivity measuring instrument in the passage for discharging the treated water from the dealkalization chamber or provided with at least one cation exchange membrane between an anode chamber and a cathode chamber and an electric conductivity measuring instrument in the passage for discharging the treated water from the anode chamber and measures the electric conductivity of the treated water to detect the leakage of a cooling water (seawater).

The present invention relates to an improvement of this previously proposed apparatus for detecting anions in water.

DISCLOSURE OF THE INVENTION

Namely, the present invention relates to an apparatus for detecting anions in water with the use of an electric conductivity cell which comprises an electrolyzer constituted by an anode chamber having an anode plate and a cathode chamber having a cathode plate via a cation exchange membrane, a direct-current power unit for applying a direct-current voltage between the anode and the cathode of the electrolyzer and an electric conductivity cell for measuring the electric conductivity of a sample water, and a flow passage for introducing the sample water into the anode chamber and a treated water flow passage for discharging the treated water which has been subjected to electrolytic treatment in the anode chamber which are connected to the anode chamber of the electrolyzer, respectively, and the treated water flow passage being connected to the cathode chamber via the electric conductivity cell.

Further, the present invention relates to a method for detecting anions in water by measuring an electric conductivity which comprises introducing a sample water into the anode chamber of an electrolyzer constituted by an anode chamber having an anode plate and a cathode chamber having a cathode plate via a cation exchange membrane, applying a direct-current voltage between the anode and the cathode to effect electrolytic treatment, then withdrawing the treated water out of the anode chamber, measuring the electric conductivity of the treated water out of the anode chamber to detect anions in the water and then, introducing the treated water into the cathode chamber of the electrolyzer.

| | |
|---|---|
| 21: boiler, | 22: superheater, |
| 23: high pressure turbine, | 24: reheater, |
| 25: low pressure turbine, | 26: generator, |
| 27: condenser, | 28: seawater, |
| 29: demineralizer, | 30: low pressure heater, |
| 31: deaerator | 32: high pressure heater, |
| 33: economizer | |

BEST MODE FOR PRACTICING THE INVENTION

The present invention will now be explained in detail with the use of the Drawings.

Figure 1:
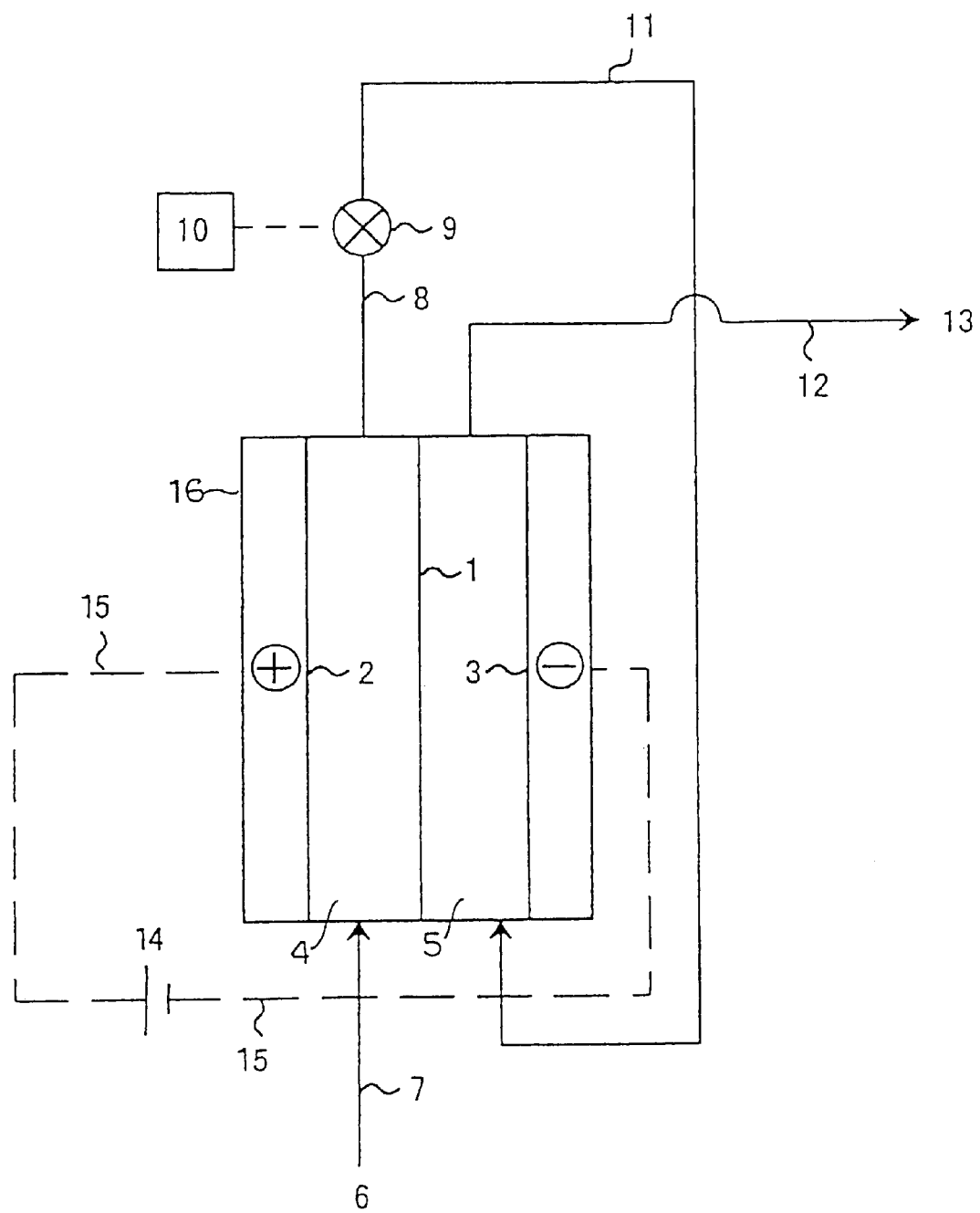
FIG. 1 is a schematic block diagram showing one example of an apparatus for detecting anions in water according to the present invention.

FIG. 1 is a schematic block diagram showing one example of an apparatus for detecting anions in water of the present invention.

In FIG. 1, an electrolyzer 16 is constituted by forming an anode chamber 4 having an anode 2 and a cathode chamber 5 having a cathode 3 via a cation exchange membrane 1. Each electrode is connected to a direct-current power unit 14 by a lead 15. A conduit 7 for introducing a sample water 6 into the anode chamber 4 is connected to the lower part of the anode chamber. Further, a conduit 8 for withdrawing the treated water which has been subjected to electrolytic treatment in the anode chamber is connected to the upper part of the anode chamber 4. An electric conductivity cell 9 is fixed to the conduit 8. The electric conductivity cell 9 is connected to an electric conductivity meter 10 which measures the electric conductivity of the treated water. The water coming out of the conductivity cell 9 is then introduced into the lower part of the cathode chamber 5 of the electrolyzer by a conduit 11. A conduit 12 is connected to the upper part of the cathode chamber 5 and through this conduit 12, the water having been treated in the cathode chamber is discharged as waste water 13 out of the system.

Next, the basic principle of the preset invention will be explained.

Figure 2:
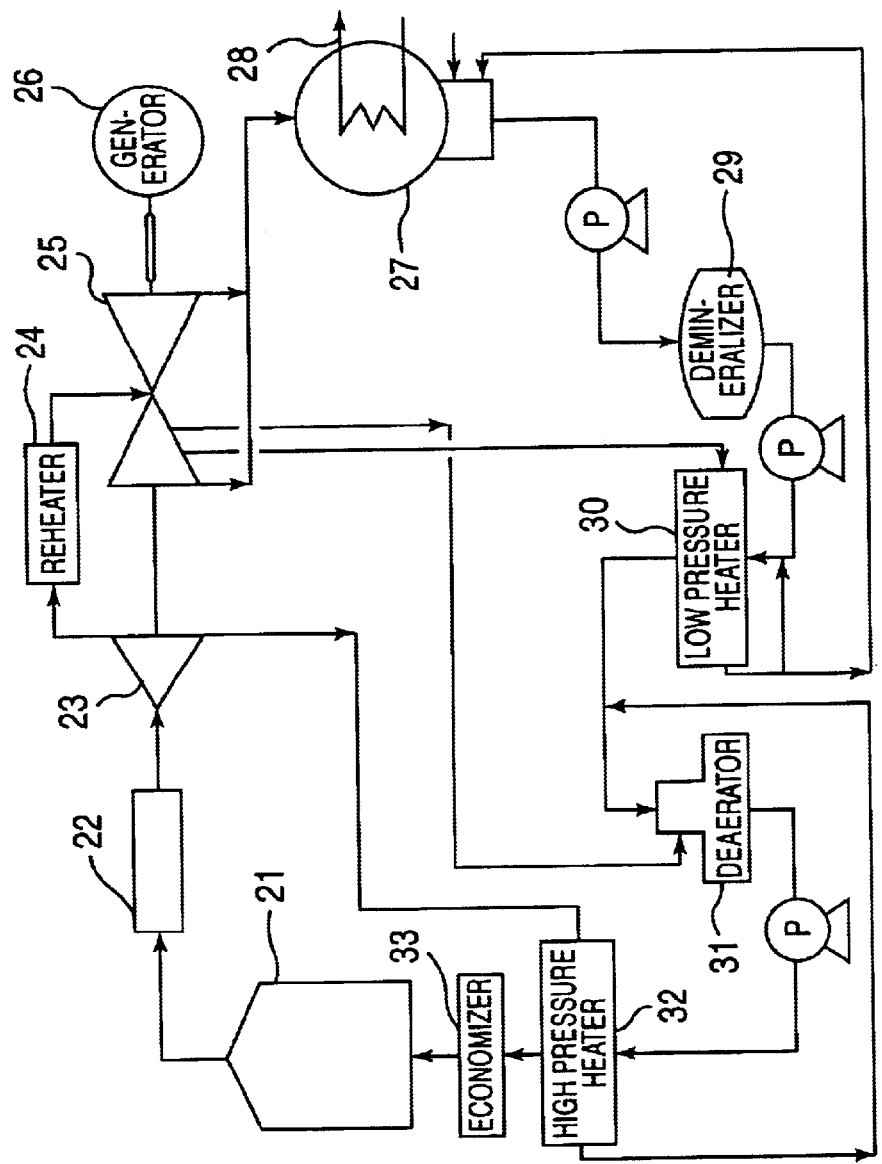
FIG. 2 is a flow diagram of the water circulation of a boiler feedwater in a thermal power station. Further, the reference numbers in FIG. 2 show the following elements, respectively.

The present invention is basically a combination of an electrodialyzer and an electric conductivity meter. In the circulatory system of a boiler water in FIG. 2, ammonia and hydrazine are added to prevent the corrosion in the system. Normally, the ammonia concentration is about 1 ppm, and the hydrazine concentration is about 0.1 ppm.

As shown in FIG. 1, a sample water 6 containing ammonia and hydrazine flows into the anode chamber 4, and upon applying a voltage between the both electrodes, part of ammonium ions and the hydrazine which are cations passes through a cation exchange membrane 1 to migrate into the cathode chamber. Accordingly, the outlet water of the anode chamber 4 comes to pure water and the measured value of the electric conductivity in the electric conductivity cell 9 becomes not greater than 0.1 $\mu$s/cm.

Here, when seawater leakage occurs in the condenser 27 (FIG. 2), in addition to the above described ammonia and hydrazine, salts such as NaCl and $Na_2SO_4$ are mixed into the circulating water. When the sample water 6 into which such salts have been mixed flows into the anode chamber 4, part of ammonium ions and the hydrazine which are cations and sodium ions pass through the cation exchange membrane 1 to migrate into the cathode chamber 5. As the result, $Cl^-$ ions and $SO_4^{2-}$ ions remain in the sample water 6 in the anode chamber 4 to form hydrochloric acid and sulfuric acid.

The electric conductivities of hydrochloric acid and sulfuric acid are greater than those of respective neutral salts and accordingly, their detection becomes possible with a high sensitivity. For example, the acid electric conductivity of a sample water containing only ammonia and hydrazine is normally not greater than 0.1 $\mu$s/cm, while that becomes greater than 1 $\mu$s/cm when seawater leakage has occurred and thus, the seawater leakage can readily be detected.

After measurement of the electric conductivity, the sample water 6 is introduced into the lower part of the cathode chamber 5 by a conduit 11. In the cathode chamber 5, part of ammonium ions and the hydrazine and sodium ions migrate from the anode chamber 4 to the cathode chamber 5 through the cation exchange membrane 1, but anions cannot pass through the cation exchange membrane Therefore, anions is retained as such in the sample water in the cathode chamber. On that account, the ionic components in the cathode chamber are returned to the same components as those of the initial sample water.

According to the apparatus shown in Japanese Patent Publication (Kokai) JP-A-9-210943 as illustrated above, a sample original water is introduced into both anode and cathode chambers, and thus, the outlet waters from respective chambers are increased in the concentration of either cations or anions and have to be subjected to treatment when discharged out of the system. However, in the apparatus of the present invention, the components of the sample water to be introduced into the apparatus are the same as those to be discharged from the apparatus and thus, the treatment of the water to be discharged is not required at all. Moreover, compared to the apparatus described in Japanese Patent Publication (Kokai) JP-A-9-210943, the apparatus of the present invention uses only half of the sample water necessary for the measurement of electric conductivity and thus, is economical.

The present invention will now be concretely explained by an example which is not construed to limit the present invention.

Example 1

With the use of the apparatus according to the flow chart shown in FIG. 1, an experiment was performed.

With a sample water prepared by adding an ammonia water to pure water having been treated with mixed bed ion exchange resins to adjust the concentration of $NH^{4+}$ to 1.1 ppm and with sample waters prepared by adding sodium chloride to the above described sample water to adjust the concentration of NaCl to 0.1 ppm, 1 ppm and 10 ppm, respectively, the electric conductivities:of the outlet waters from the anode chamber were measured.

The electrodes had a size of 50 (in width)×400 (in height) mm, and the distance between the electrodes was set at 2 mm and a cation exchange membrane was placed between the anode and the cathode and fixed with a rubber packing. A 100 V direct-current was applied between the anode and the cathode, and each sample water was passed at a rate of 300 ml/min.

As the result, with the sample water added with the ammonia water alone, the electric conductivity of the outlet sample water from the anode chamber was 0.078 $\mu$s/cm. With the sample water further added with NaCl at a concentration of 0.1 ppm, the electric conductivity of the outlet sample water from the anode chamber was 0.71 $\mu$s/cm; with the sample water further added with NaCl at a concentration of 1 ppm, the electric conductivity of the outlet sample water from the anode chamber was 6.98 $\mu$s/cm; and with the sample water further added with NaCl at a concentration of 10 ppm, the electric conductivity of the outlet sample water from the anode chamber was 64 $\mu$s/cm. These values were approximately in accord with the theoretical electric conductivity values when the entire NaCl has been converted into HCl. Thus, it has been found that when seawater has leaked into a sample water containing ammonia, the seawater leakage can be detected with an extremely high sensitivity in a short period of time.

INDUSTRIAL APPLICABILITY

The present invention can measure trace amounts of a chlorine ion in an alkali solution which does not contain anions except an hydroxide ion and can, as the advantage, continuously measure them without requiring replacement of the resins whose ion exchange capacity has decreased compared to the conventional method which uses cation exchange resins. Further, the apparatus of the present invention can effect detection with a sensibility higher than that of a sodium monitor and is an extremely inexpensive salt detecting apparatus compared to the other instruments for analysis. Additionally, even in comparison with the apparatus shown in Japanese Patent Publication (Kokai) JP-A-9-210943, the apparatus of the present invention does not require the treatment of the water to be discharged and can advantageously reduce the necessary amount of a sample water to half.

Thus, the present invention can be utilized in detecting the leakage of the cooling water of a condenser with a high sensitivity, particularly in a thermal power station and a nuclear power station.

What is claimed is:

1. An apparatus for detecting anions in water with the use of an electric conductivity cell, which comprises an electrolyzer constituted by an anode chamber having an anode plate and a cathode chamber having a cathode plate via a cation exchange membrane, a direct-current power unit for applying a direct-current voltage between the anode and the cathode of the electrolyzer, and an electric conductivity cell for measuring the electric conductivity of a sample water, and a flow passage for introducing the sample water into the anode chamber and a treated water flow passage for discharging the treated water which has been subjected to electrolytic treatment in the anode chamber of the electrolyzer which are connected to the anode chamber, respectively, and the treated water flow passage being connected to the cathode chamber via the electric conductivity cell.

2. The apparatus for detecting anions in water according to claim 1 further comprising a filter for removing cruds and fine particles in a sample water in the flow passage for introducing the sample water into the anode chamber.

3. A method for detecting anions in water by measuring an electric conductivity which comprises introducing a sample water into the anode chamber of an electrolyzer constituted by an anode chamber having an anode plate and a cathode chamber having a cathode plate via a cation exchange membrane, applying a direct-current voltage between the anode and the cathode to effect electrolytic treatment, withdrawing the treated water out of the anode chamber, measuring the electric conductivity of the treated water out of the anode chamber to detect anions in the water and then, introducing the treated water into the cathode chamber of the electrolyzer.

4. The method for detecting anions in water according to claim 3 further comprising subjecting the sample water before introducing it into the anode chamber to pretreatment to remove cruds and fine particles therefrom.

5. A method for detecting anions in water according to claim 3 wherein all of the treated water withdrawn from the anode chamber is introduced into the cathode chamber.

\* \* \* \* \*